United States Patent
Saotome et al.

(10) Patent No.: US 9,861,445 B2
(45) Date of Patent: Jan. 9, 2018

(54) PORTABLE DEVICE FOR IDENTIFICATION OF SURGICAL ITEMS WITH MAGNETIC MARKERS, METHOD FOR IDENTIFYING SURGICAL OBJECTS WITH MAGNETIC MARKERS AND SYSTEM FOR THE PREVENTION OF RETENTION OF SURGICAL ITEMS WITH MAGNETIC MARKERS

(71) Applicant: INSTITUTO TECHNOLÓGICO DE AERONÁUTICA—ITA, São José dos Campos (BR)

(72) Inventors: Osamu Saotome, São José dos Campos (BR); Rogério Dos Santos Vagner, São Paulo (BR); Carlos Fonseca Pereira Evaldo, São Paulo (BR); José Elias Matieli, São José dos Campos (BR)

(73) Assignee: INSTITUTO TECHNÓLOGICO DE AERONÁUTICA—ITA, São José Dos Campos ( * ) Notice: Subject to any disclaimer, the term of this patent is extended or adjusted under 35 U.S.C. 154(b) by 0 days.

(21) Appl. No.: 14/771,360

(22) PCT Filed: Feb. 27, 2014

(86) PCT No.: PCT/BR2014/000069
§ 371 (c)(1),
(2) Date: Oct. 3, 2015

(87) PCT Pub. No.: WO2014/131100
PCT Pub. Date: Sep. 4, 2014

(65) Prior Publication Data
US 2016/0008091 A1  Jan. 14, 2016

(30) Foreign Application Priority Data
Feb. 28, 2013 (BR) .................. 102013004787 U (51) Int. Cl.
G08B 13/14 (2006.01)
A61B 19/00 (2006.01)
(Continued)

(52) U.S. Cl.
CPC .............. *A61B 19/54* (2013.01); *A61B 90/39* (2016.02); *A61B 90/90* (2016.02); *A61B 90/98* (2016.02);
(Continued)

(58) Field of Classification Search
CPC ......... A61B 19/54; A61B 90/39; A61B 90/90; A61B 90/98; A61B 2090/0804;
(Continued)

(56) References Cited

U.S. PATENT DOCUMENTS 4,660,161 A  *  4/1987  Okada .................... G01C 17/38
33/356
5,331,244 A    7/1994  Rabe
(Continued)

OTHER PUBLICATIONS

International Search Report issued in International PCT Application No. PCT/BR2014/000069; dated May 22, 2014.

*Primary Examiner* — Zhen Y Wu
(74) *Attorney, Agent, or Firm* — Pearne & Gordon LLP (57) ABSTRACT

The present invention refers to a portable device for identification of surgical items with magnetic markers, method for identifying surgical objects with magnetic markers and system for the prevention of retention of surgical items with magnetic markers. The present invention can be used in surgical centers, with the aim of detecting surgical elements/objects (5) retained in the patient after surgery. The present invention aims to provide instrumental support in object location surgical (5) retained inside the body cavities for (Continued)

detecting artifacts forgotten after a surgical procedure, by means of device and specific objects and method and system for their identification.

12 Claims, 8 Drawing Sheets

(51) Int. Cl.
| | |
|---|---|
| *G06K 7/10* | (2006.01) |
| *G08B 13/24* | (2006.01) |
| *A61B 90/90* | (2016.01) |
| *A61B 90/98* | (2016.01) |
| *G01V 15/00* | (2006.01) |
| *A61B 90/00* | (2016.01) |

(52) U.S. Cl.
CPC ..... *G06K 7/10366* (2013.01); *G08B 13/2462* (2013.01); *A61B 2090/0804* (2016.02); *A61B 2090/0805* (2016.02); *A61B 2090/3958* (2016.02); *G01V 15/00* (2013.01)

(58) Field of Classification Search
CPC .... A61B 2090/0805; A61B 2090/3958; G06K 7/10366; G08B 13/2462
USPC ...................................... 340/572.1
See application file for complete search history.

(56) References Cited

U.S. PATENT DOCUMENTS

| | | | | |
|---|---|---|---|---|
| 5,879,297 A | * | 3/1999 | Haynor ............... | A61B 5/06 128/899 |
| 5,902,238 A | * | 5/1999 | Golden ............... | A61B 5/06 128/899 |
| 6,026,818 A | | 2/2000 | Blair et al. | |
| 8,988,225 B2 | * | 3/2015 | Smith ............... | G08B 13/08 340/572.1 |
| 9,207,315 B1 | * | 12/2015 | Plautz ............... | G01S 13/885 |
| 2002/0158761 A1 | * | 10/2002 | Runyon ............... | G07C 5/008 340/539.1 |
| 2003/0129995 A1 | * | 7/2003 | Niwa ............... | H04M 1/72522 455/456.1 |
| 2003/0164766 A1 | * | 9/2003 | Britton ............... | G01V 3/105 340/552 |
| 2004/0222789 A1 | * | 11/2004 | Pinsky ............... | G01N 27/72 324/261 |
| 2006/0149186 A1 | * | 7/2006 | Wantink ............... | A61M 25/10 604/96.01 |
| 2007/0056582 A1 | * | 3/2007 | Wood ............... | A61B 5/0059 128/200.24 |
| 2007/0123772 A1 | * | 5/2007 | Euliano ............... | A61B 5/073 600/407 |
| 2007/0202956 A1 | * | 8/2007 | Ogasawara ............ | G06F 1/1624 463/46 |
| 2007/0214386 A1 | * | 9/2007 | Watanabe ............ | G06F 11/2284 714/13 |
| 2011/0163854 A1 | * | 7/2011 | Hamelin ............ | A61B 19/5244 340/10.1 |
| 2011/0190579 A1 | * | 8/2011 | Ziarno ............... | A61B 1/00016 600/109 |
| 2013/0001940 A1 | * | 1/2013 | Arsenault ............ | G02B 1/005 283/67 |
| 2013/0021192 A1 | * | 1/2013 | Daly ............... | G01V 3/15 342/22 |
| 2013/0135106 A1 | * | 5/2013 | Chang ............... | G08B 13/149 340/572.1 |
| 2013/0289663 A1 | * | 10/2013 | Newman ............... | A61N 1/08 607/62 |

\* cited by examiner

PORTABLE DEVICE FOR IDENTIFICATION OF SURGICAL ITEMS WITH MAGNETIC MARKERS, METHOD FOR IDENTIFYING SURGICAL OBJECTS WITH MAGNETIC MARKERS AND SYSTEM FOR THE PREVENTION OF RETENTION OF SURGICAL ITEMS WITH MAGNETIC MARKERS

FIELD OF INVENTION

The present invention is part of the field of Electronics applied to Medicine (including Veterinary Medicine), especially in the area of Medical Physics, once it refers to a portable identification device of retained surgical objects for use in surgical centers, with the aim of detecting objects retained in patient during surgeries, especially after cavitary surgeries.

DESCRIPTION OF THE STATE OF THE ART

Electromagnetic Energy

Document U.S. Pat. No. 5,902,238 describes medical distal pipe with marker located and oriented along the pipe and equipment to locate said marker inside the body of a patient to guide the conduction of said distal tube to a specific location in the patient's body. The purpose of the method is to allow the positioning of the distal tube in the interior of the patient's body, where the magnetic dipole is located by a detection apparatus that measures the gradient of force of static magnetic field from the magnet located at the end of the distal tube with a fixed orientation along the interior of the distal tube. This method uses a generator to excite the detection field that is composed of two signals that are used jointly for the location and determination of marker orientation. Our objective is to indicate the presence of a marker in the interior of the patient's body. The proposed invention discloses a high sensitivity geomagnetic sensor properly organized in a suitable arrangement to be insensitive to the orientation of Earth's magnetic field, which detects the presence of a non-uniform perturbation caused by a magnetic marker. It, therefore, does not use activation energy, as in the method of the said prior art. The elements are different: a passive sensor instead of an active sensor; identification of the deformation of local field in an absolute manner, not aiming the determination of a specific intensity and direction.

In relation to the documents of the state of the art, with relation to the identification of electromagnetic TAGs the following documents can be evaluated: US2007/0285249; U.S. Pat. No. 6,777,623; US2004/0129279; US2003/0105394; U.S. Pat. No. 4,114,01; US2003/0105394 A1; US 2004/0129279; US2010/262433-A1; U.S. Pat. No. 7,996,286-B2; WO2005035007 (A2)/2005 May 3-21; WO2005035007 (A3) 2005 Dec. 15; WO2005035007 (A2)/ 2005 May 3-21; WO2005035007 (A3) 2005 Dec. 15; PCT/US91/07124; WO93/05708/1993 Apr. 1; U.S. Pat. No. 7,787,931, WO2006060781A1 and U.S. Pat. No. 5,842,986A.

Document US 2007/0285249 A1—Method, apparatus and article for detection of transponder tagged objects, for example during surgery—refers to post-surgery retained object identifiers based on the acquisition of information generated by tags that are sensitive to magnetic fields. The document claims the use of several radio frequencies for the tags. The disadvantages of this document refer to the need of a previous manufacturing system of tags, which increases invention deployment cost and obliges health institutions to constantly buy new programed tags; another disadvantage of the invention described in this document is that the device requires a table with wheels, which, inside a surgical and post-surgery center, would be an additional apparatus to be used, transported and connected, even for a short period of time, that might cause a restriction of use of the equipment by the team, especially in surgical centers that have limited space.

Document US 2004/0129279 A1—Miniature magneto-mechanical tag for detecting sponges and implements—describes identifiers of post-surgery retained objects based in preparation of tags, which are sensitive to magnetic fields in the frequency range of 70 to 300 kHz. Among the disadvantages of this document, we highlight the requirement of tags to be previously manufactured what makes its implementation more expensive, further obligating the hospital to always buy pre-programmed tags. To perform the implementation of the invention, health institutions will require an adequate place for this purpose with separate buildings and electrical installations, as well as an apparatus maintenance system.

Document US2003/0105394 A1—Portable surgical implement detector—describes a solution of post-surgery retained object identifiers based on adhesion or attachment of tags that are sensitive to magnetic fields that, under its influence, come into oscillation allowing their detection and identification. The document claims the use of several radio frequencies for the tags. Among the disadvantages of this document, we highlight the requirement of tags to be previously manufactured what makes its implementation more expensive, further obligating the hospital to always buy pre-programmed tags. Another disadvantage of this invention is that it requires a table with wheels that within a surgical center would be an apparatus difficult to transport or handle.

Documents US2010262433-A1; U.S. Pat. No. 7,996,286-B2—Method, system and products for tracking surgical items—describe a system to capture information generated by tags that are sensitive to magnetic fields. These systems offer the restriction of being made of high cost materials that impact in the system total cost.

Documents WO2005035007 (A2)/2005 May 3-21; WO2005035007 (A3) 2005 Dec. 15—Attachment of electronic tags to surgical sponges and implements—describe a solution of identifiers of post-surgery retained objects. It is based on the adhesion or attachment of tags that are sensitive to magnetic fields that under its influence come into oscillation allowing their detection and identification. The document claims the use of several radio frequencies for the tags. Among the disadvantages of this document, we highlight the requirement of tags to be previously manufactured what makes its implementation more expensive, further obligating the hospital to always buy pre-programmed tags.

Document 100 14542 A1/Dec. 13, 2001—Erfassungassystem und Erfassungsverfahren für chirurgische Instrumente und Materialien—describes a system based on the acquisition of information generated by tags sensitive to magnetic fields. Among the disadvantages of this document, we highlight the requirement of tags to be previously manufactured what makes its implementation more expensive, further obligating the hospital to always buy pre-programmed tags.

Document US2006/0150990A1/13 Jul. 2006—Equipment for the detection of surgical products—describes a product based on the acquisition of information generated by metallic materials submitted to electromagnetic signal.

Among the disadvantages of this document, we highlight the requirement of tags to be previously manufactured what makes its implementation more expensive, further obligating the hospital to always buy pre-programmed tags.

Document PCT/US91/07124/WO93/05708/1993 Apr. 1—Surgical instrument detector utilizing a powered marker—describes a solution of identifiers of post-surgery retained objects. It is based on the adhesion or attachment of tags sensitive to magnetic fields that under its influence oscillate, allowing their detection and identification. The document claims the use of several radio frequencies for the tags. Among the disadvantages of this document, we highlight the requirement of tags to be previously manufactured what makes its implementation more expensive, further obligating the hospital to always buy pre-programmed tags.

Document U.S. Pat. No. 7,787,931—Portable Surgical Implement Detector—describes detectors of post-surgery retained objects in cavities. It is based on adhesion or attachment of passive tags sensitive to electromagnetic fields that under their influence change their impedance allowing their detection by means of a portable detection unit located in a first room next to the surgical procedure. The presence of retained object is indicated by sonorous or luminous signalization. Among the existing problems in the document U.S. Pat. No. 7,787,931, it can be highlighted that the used detection method causes electromagnetic interference to other medical equipment and instruments, being suggested their shielding; the invention requires patient displacement from the surgery room to another room adapted to surgical object localization procedure, which is a disadvantage, further adding risk to the patient; with only partial (limited) portability, considering that the detection and indication units are physically separated; additionally, there is the fact of need of use of a marker with some constructive complexity and relatively high cost, considering that it is a miniaturized electronic circuit.

Document WO2006060781A1—Radio Frequency Identification for Medical Devices—describes a system to identify medical objects during the stage of preparation of a surgical procedure based on the use of reader and radio frequency identification tag (RFID), without being necessary violation of the sealed package where the referred medical objects are stored. The RFID identification tag is a passive device and comprises an electromagnetic energy receiving and data transmitting antenna, and an integrated circuit, while the RFID reader comprises an electromagnetic energy transmitter antenna and data receiver, a processor and a display. The system is based on adhesion or attachment to the sealed package and its reading by RFID reader. The system operates at integrated circuit activation by the RFID reader antenna, which, transmitting electromagnetic energy activates the tag that responds, sending data in the form of a sequence of electromagnetic signals to the RFID reader. The received data are processed, generating the information that will be presented on the display of the RFID reader. Among document WO2006060781A1 existing problems, it can be highlighted that, by comprising the antenna, the said tag has dimensions that precludes its use as a marker of surgical objects to be used in surgical procedures. Such procedures require insertions of surgical object in small cavities or incisions in the patient's body. In addition, the tag has certain constructive complexity and relatively high cost, considering that it is a miniaturized electronic circuit.

Document U.S. Pat. No. 5,842,986A—Ferromagnetic Foreign Body Screening Method and Apparatus—describes a method and apparatus for locating a ferromagnetic body within a prospection region. This method is based on the application of a low power magnetic field in a host prospection area and sensing magnetic field of a ferromagnetic object retained inside the prospection region. A field excitation coil is designed to create a region of finite magnetic field in the prospection region and an almost null magnetic field region. The sensors are positioned in the interior of almost zero magnetic field region to minimize the effects of the applied magnetic field, which are additionally reduced by introduction of a reference sensor, field compensation coils and feedback system. The field gradient measured by the sensors is processed to locate and characterize the ferrous object. Among the disadvantages of this method, we can list spatial limitation of object location system, need of generation of magnetic field excitation and compensation; and complex system for the canceling of this field in the region of identification of ferromagnetic object.

Optical

The state of the art for the identification with optical and/or combined technology can be seen in documents: US 2009/0317002 A1 Dec. 24, 2009; US2007268133 (A1) September 30/-22; U.S. 7,557,710 (B2) 2009 Jul. 7.

Document US 2009/0317002 A1 Dec. 24, 2009—Intraoperative system for identifying and tracking surgical sharp objects, instruments, and sponges—refers to an identification system based on the recognition of optical "tags", including bar codes, which by means of image capture systems, can track and identify the used materials. Several types of tags can be used, materials disposal boxes, discard wrappings and support carts, these can be monitored with the installation of lights and cameras. Among the disadvantages of this system, we can highlight the high operational costs of a surgical procedure, maintenance costs and operational control.

Documents US2007268133; US 2009/0317002 A1 September 30/-22; U.S. Pat. No. 7,557,710 (B2) 2009 Jul. 7—System for tracking surgical items in an operating room environment—describe an identification system which combines optical with RF system. Among the disadvantages of this document, we highlight the requirement of tags to be previously manufactured what makes its implementation more expensive, further obligating the hospital to always buy pre-programmed tags. In addition, the costs of installation and maintenance are high.

Radiopaque

For the assessment of the state of the art in the field of identification with radioactive elements see what is described in U.S. Pat. No. 6,777,623 B2 Aug. 17, 2004:

U.S. Pat. No. 6,777,623 B2—System and method of tracking surgical sponges—describes a system of identification that uses radiopaque markers added to gauzes and or to cloths used in surgical procedures, after its use. The disadvantages of the state of the art are related to the fact that the implementation of the present invention increases surgical procedures operating costs as well as expenditure with maintenance and operational control. Another disadvantage of this invention is that it requires a table with wheels, which, within a surgical center, would be difficult to transport or would restrict the operational space in the surgical center.

Magnetic Material

Document U.S. Pat. No. 4,114,601 Sep. 19, 1978—Medical and surgical implement detection system—describes a system of identification with the use of transponders manufactured with a composition of ferrite; with this material, devices are manufactured sensitive to magnetic field variations, these devices can be manufactured with a specific polarization. Based on its polarized characteristic, the device is detected when exposed to a magnetic field. Among the disadvantages, we can highlight the fact that it requires the manufacture of a specific material already patented.

Trackers by RF

Documents GB2436707-A; JP2007/260395-A; US2007/238980-A1; U.S. Pat. No. 7,471,202-B2—Medical electromagnetic tracking system for use by e.g. surgeon, has image-capture component e.g. surgical microscope, including electromagnetic receiver, where receiver is conformally attached or mounted to component—describe a receiver that detects signals from one electronic tracker that analyzes the signals to identify and determine transponder position. Among the disadvantages, we can highlight the fact that it requires the manufacture of a specific material already patented.

Active RFID

Documents WO2009/151946-A2; US2009/315681-A1; WO2009/151946A3—Surgical object detection and identification system for medical provider, has identification and presence/absence transponders that are coupled to each other to form integral detection and identification transponder—describe a system that has an identification transponder transmitting an identification signal in response to an interrogation signal. Among the disadvantages, we can highlight the fact that it requires the manufacture of a specific material.

Inductive

Document U.S. Pat. No. 5,188,126 (A)—Surgical instrument detector utilizing capacitive coupling—describes a system of identification with the use of transponders, and detector based on inductive loop antenna with capacitive coupling to the marker inserted into the fabric. Among the existing problems in this instrument, we can highlight the need for a system of previous manufacturing of the tags, which increases its cost and requires the hospital to always buy pre-programmed tags. In addition, the costs of installation and maintenance are high.

UWB

Document PCT/US2004/035774/WO2005/044085/2005 May 3-19—Surgical instrument detector utilizing a powered marker—describes a system that uses UWB Ultra Wide Band. Among the problems, we can highlight the installation and training costs to its use, and in addition, customization of the building of the surgical center.

Advantages of the Invention

The present invention solves the problem of buying on demand tags and also solves the problems of resistance to sterilization temperature, portability and fast use, it can be sterilized by methods used in the medical area, it meets public health system cost needs, the materials used can be recycled, it reduces operational costs because it does not require skilled labor, it increases the quality of the procedure regarding tired manpower after long surgeries, it does not use previously patented device, it does not require alterations and or installations in the surgical room.

BRIEF DESCRIPTION OF THE INVENTION

The present invention refers to a portable identification device, surgical objects with magnetic markers, identification method of surgical objects with markers and prevention system of retention of surgical objects with magnetic markers. The present invention can be used in surgical centers, with the objective of detecting surgical elements/objects retained in the interior of the patient after surgery.

The present invention aims to provide instrumental support in finding surgical objects retained inside body cavities for detecting artifacts forgotten after a surgical procedure, by means of device and specific objects and method and system for their identification.

The present invention was developed in view of the need to develop a relatively low cost and easy-to-use solution, which could be incorporated into the public and private surgical services, with the objective of reducing the number of objects retained after cavitary surgery.

The present invention was conceived with the objective of providing surgical and health system management teams with a low cost application-easy tool, without need of specialized training (basically, to operate the equipment it is only necessary to scan its simplified operation manual), to detect the presence of any surgical objects retained, ferromagnetic or not.

Currently, one of the most used ways of surgical objects control in a surgical procedure is the count and conference by the nurse and surgeon present in the act.

It is important to mention that "TAG" can be understood, in a generic way, as any element, embedded, for example in a product or object, that can function as signaling or identifying means of the presence of objects to be tracked. As a simplified example, we can mention a Radio Frequency Identification Device (RFID) TAG for a book in a specialized publication shop. TAG's can be made of various types, ferromagnetic, optical, inductive, capacitive, radiopaque, isotopes, and chemical marker.

DETAILED DESCRIPTION OF THE INVENTION

The present invention refers to a portable identification device, surgical objects with magnetic markers, retention prevention system of surgical objects with magnetic markers and identification method of objects with surgical magnetic markers and can be used in surgical centers, with the objective of detecting surgical elements/objects (5) retained in patient after surgery.

Portable Identification Device (1)

The portable identification device (1) comprises: a handhold (7); power source (11); push button on/off switch (10); luminous alarms (8); circular pins for electrical contact (12); sensing surface (3); programmable logic device; sound alarms; electronic warning device (2).

The device (1) can additionally contain protective film of latex and a button to enable/disable the sound alarm (9). The device can be viewed by means of its graphic representation as is presented in FIGS. 1A, 1B, 2A, 2B, 7, 8, 9, 10, 11, 12, 13 and 14.

The device (1) has, preferably, the shape of a tennis paddle and has, preferably, in its handhold (7) a compartment to accommodate a power source (11), which may or may not be rechargeable.

The device further needs a charge base.

The power source (11) may be, for example: a battery, a super capacitor, an AC-DC converter, among other types of electric power source.

A push button on/off switch (10), allowing to connect and disconnect the device (1), is preferably located under protective film.

The programmable logic device can be: microprocessor, microcontroller, microprocessor and/or microcontroller; CPLD (Complex Programmable Logic Device); FPGA (Field Programmable Gate Array); PAL (Programmable Array Logic) and ASIC (Application Specific Integrated Circuit).

Figure 1A:
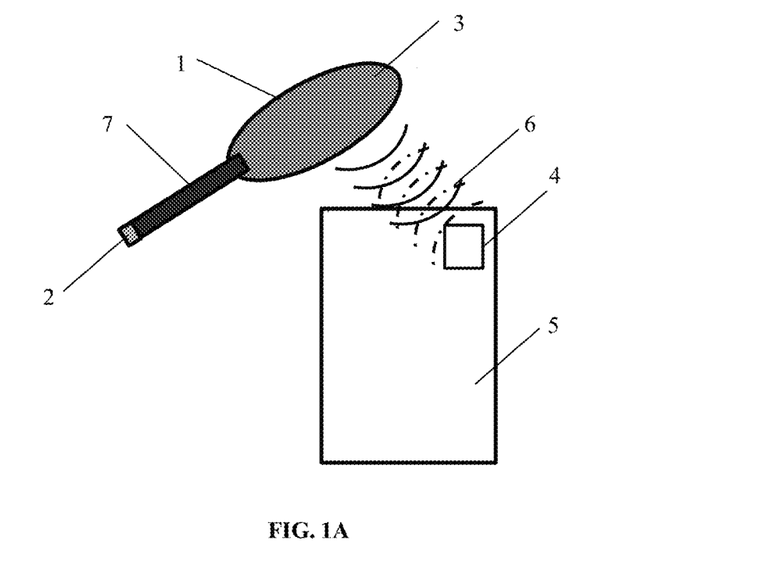
FIG. 1A is a schematic representation of the identification equipment of retained surgical object. They are indicated: 1, portable identification device; 2, electronic warning device; 3, sensing surface; 4, magnetic marker; 5, retained object; 6, magnetic field generated by the presence of magnetic marker (4); 7, handhold.
Figure 1B:
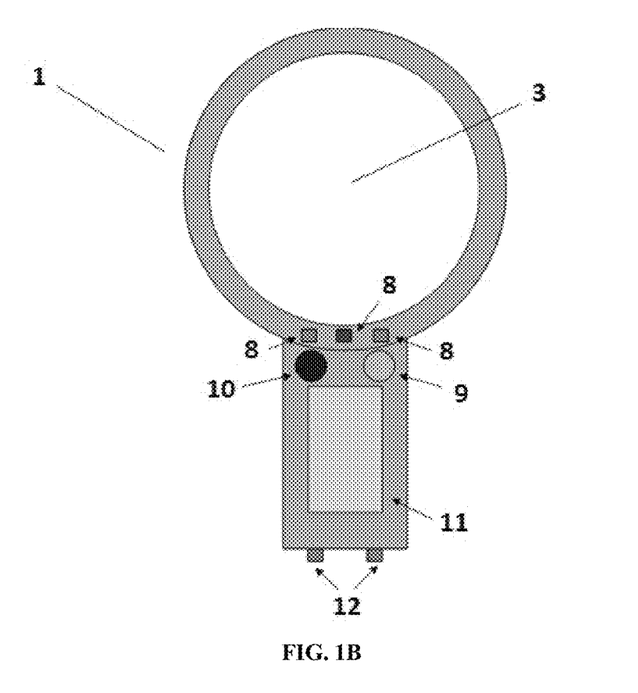
FIG. 1B is a schematic representation of the identification equipment of retained surgical object. They are indicated: 1, portable identification device; 3, sensing surface; 8, luminous alarms; 9, sound alarm; 10, on/off switch button; 11, power source; 12, circular pins for electrical contact.

Luminous alarms (8) of the device (1) are preferably LED and are located, preferably, at the top end of the handhold (7) and vary between two and three, and are preferably, in number of three, as shown in FIG. 1B. Luminous alarms (8) indicate that the probe is on; that there is a retained object (5); and/or that the power source (11) is discharged. Preferably, the left alarm light (8) indicates that the probe is on, the central light alarm (8) indicates the presence of retained object (5) in the prospection field and the right light alarm (8) indicates that the power source (11) is discharged.

The electronic warning device (2) is a transducer, which activates, preferably, audible and luminous alarms.

When the power source (11) is at critical level, preferably, a sound stimulus of variable cadence indicates the need for recharging.

Preferably, at the base of the handhold (7), there are plugs for access to electrical power source system (11), providing electrical contact to power source charger (11).

The device (1) is portable and small in size, not occupying too much space in the surgical center. Its approximate dimensions vary from 100×75×15 mm to 600×400×300 mm, preferably, 300×200×150 mm.

The sensing surface (3) is located preferably, in the circular area of the portable identification device (1), as can be seen in FIGS. 1A, 1B, 2A and 2B. The sensing surface (3) is composed of the sensing elements, which identify the magnetic markers (4). The sensing surface (3) of the portable identification device (1) senses presence of marker by means of disturbance generated on geomagnetic sensor elements by the magnetic field (6) of the magnetic marker, which alter the electrical characteristics of a measurement bridge providing electrical signal to be measured by a microcontroller or microprocessor system.

Figure 2A:
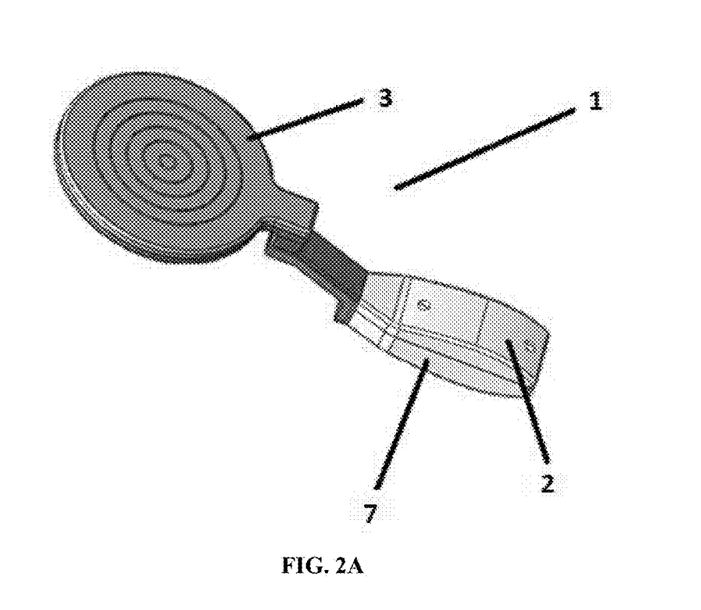
FIG. 2A is a device bottom schematic representation, showing the sensing surface side directed to the field. It is shown: 1, portable identification device; 2, electronic warning device; 3, sensing surface; 7, handhold.
Figure 2B:
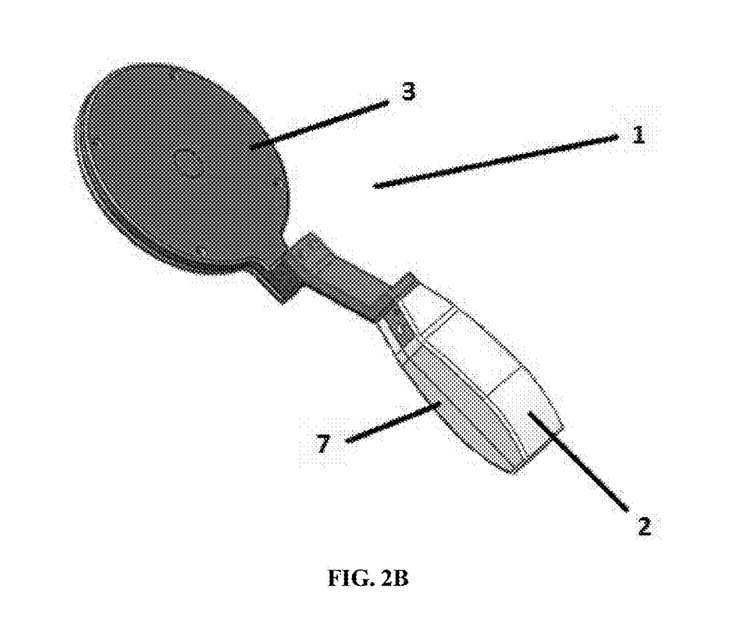
FIG. 2B is a device top schematic representation, showing sensing surface side that directed to the user. It is shown: 1, portable identification device; 2, electronic warning device; 3, sensing surface; 7, handhold.

Electrical signal disturbance generated by the magnetic field (6) of the magnetic marker is compared by programmable logic device with security levels and after repeated measurements and disparity between values confirmed, programmable logic device provides audible indication by means of sound stimuli in patterns that indicate the presence and approximate location of the object. additionally, object presence is also indicated via signaling, luminous alarm light blinking cadence. As can be seen in FIGS. 2A and 2B, it is the warning electronic device (2) at the end of the handhold (7), that triggers the luminous and sound alarms (8).

The device (1) is constructed in a hermetic way, allowing its sterilization by means of cleaning products after use.

The device (1) preferably operates, under its internal power source (11) and internal supervision system that alarms when it is necessary to recharge the power source, using sound and luminous signaling.

Recharging Base

Power source (11) may be rechargeable or not. In case of being rechargeable, a recharge base is necessary for power source (11) recharging. It is composed of a mechanical system where the portable identification device (1) is docked to charge the internal power source from commercial network.

The recharging base provides AC power to the charger for the internal power source (11) that is located, preferably, on portable identification device (1) handhold (7). A preferably full range AC/AC push-pull converter, provides average 5 VAC level of negative cycles as positive.

The AC/AC converter is full range from 100 to 240 VAC, and consumes 0.5 A.

The portable identification device (1) handhold (7) docks into the power source recharging base compartment and the base metallic contacts connects to the portable identification device (1) contact pins located at the handhold (7). The charging electrical circuits are current limited to prevent damage both to the charger and to the portable identification device.

Surgical Objects with Magnetic Markers

The magnetic markers (4) are made of sintered material and coated with biocompatible acrylic resin that protects the patient against contact with the material of which the markers are made. The magnetic markers (4) are attached to the surgical elements/objects (5) (as for example: surgical instruments and materials), fabrics, gauze, clothing, bandages, plastic, rubber components, tweezers, scalpels, scissors, retractors, needle holder, compresses, drains, gloves, probes, catheters, and other materials used in surgical environments.

The magnetic marker (4) does not require power to operate.

The magnetic marker (4) is manufactured, preferably, in material known as rare earth composed of Neodymium, Iron, Boron or a mixture thereof by means of a sintering process, and can be attached to surgical elements/objects (5) by chemical adhesion, mechanical attachment, or manufactured with fabrics or sewn, allowing a broad spectrum of application possibilities. The magnetic markers (4) are incorporated into the surgical elements/objects and sets (5), preferably by sewing.

Figure 3:
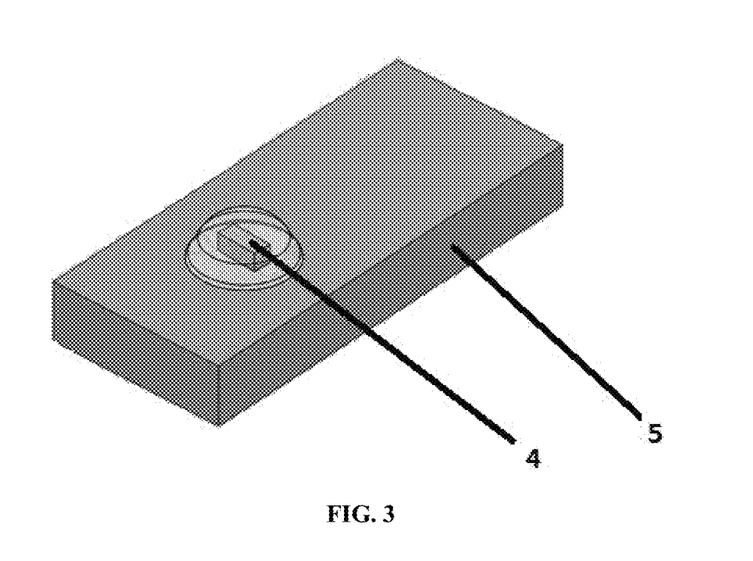
FIG. 3 is a schematic representation of chemical adhesion of magnetic marker to surgical object. It is shown: 4, magnetic marker; 5, retained object.

To attach the magnetic marker (4) to the surgical element/object and set (5), via chemical adhesion, biocompatible adhesive is used which adhere and encapsulate the magnetic marker and this is glued to surgical object, as can be seen in FIG. 3, avoiding that it be reworked after purchasing.

Figure 4:
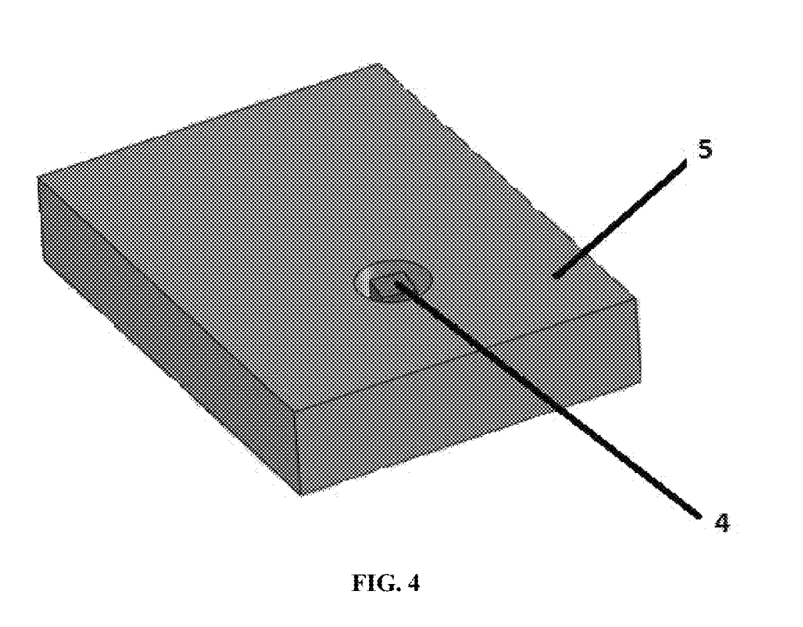
FIG. 4 is a mechanical assembly schematic representation of magnetic marker to surgical object. It is shown: 4, magnetic marker; 5, retained object.

To attach the magnetic marker (4) to the surgical element/object and set (5) via mechanical assembly the magnetic marker (4) is inserted at the time of surgical instrument manufacture, taken into account in the instrument design, or after its manufacture in a groove prepared for magnetic marker (4) insertion, as can be seen in FIG. 4.

Figure 5:
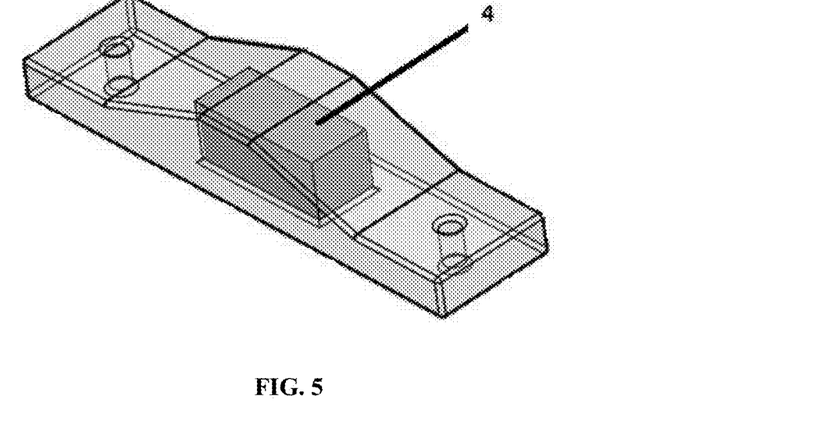
FIG. 5 is an encapsulation schematic representation of magnetic marker (4) into biocompatible resin with holes.

Two methods of attaching the magnetic markers (4) to surgical elements/objects and sets (5) via sewing, are proposed. The first possible way of marker encapsulation is its coating in biocompatible resin with holes to be stitched to the fabrics, as can be seen in FIG. 5. The second way is by manufacture of magnetic markers (4) to be preferably, sewn, darned, or incorporated into the fabric at the time of its manufacture.

Figure 6:
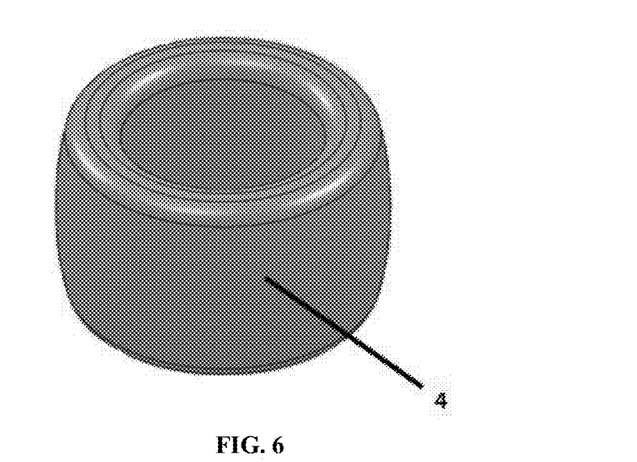
FIG. 6 is a magnetic marker schematic representation (4), manufactured specifically to be sewn in surgical fabrics.
Figure 7:
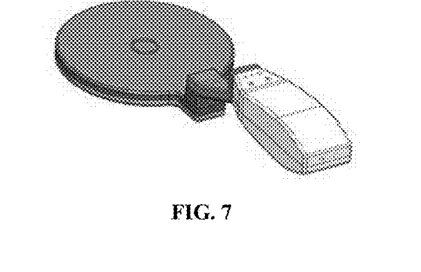
FIG. 7 is an identification device schematic representation, in perspective, of the retained surgical object.
Figure 8:
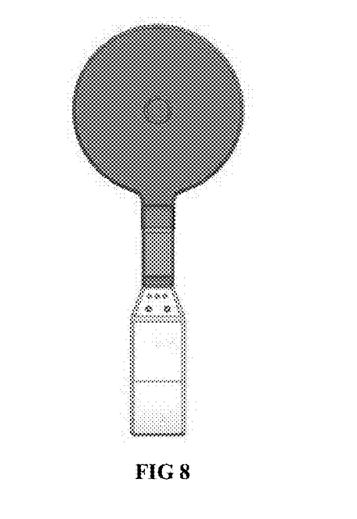
FIG. 8 is a schematic representation, in top view, of the identification device of retained surgical object.
Figure 9:
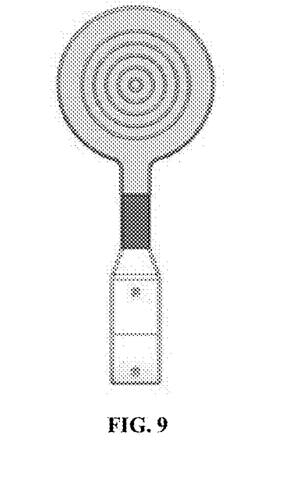
FIG. 9 is a schematic representation, in bottom view, of the identification device of retained surgical object.
Figure 10:
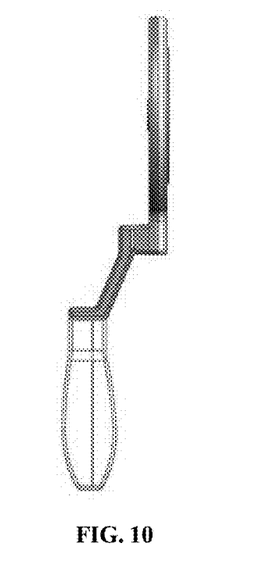
FIG. 10 is a schematic representation, in lateral view, of the identification device of retained surgical object.
Figure 11:
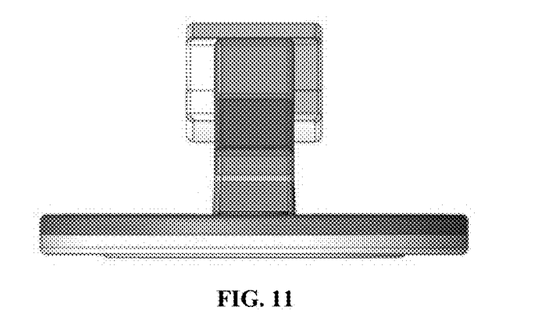
FIG. 11 is a schematic representation, in front view, of the identification device of retained surgical object.
Figure 12:
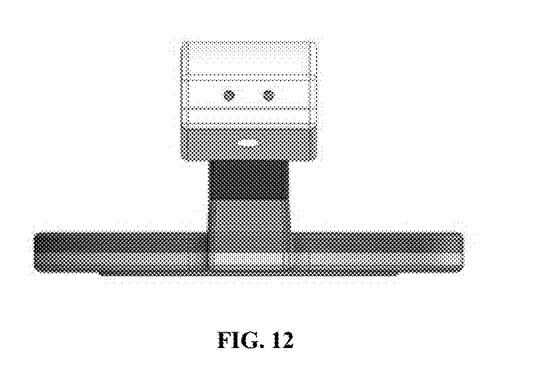
FIG. 12 is a schematic representation, in rear view, of the identification device of retained surgical object.
Figure 13:
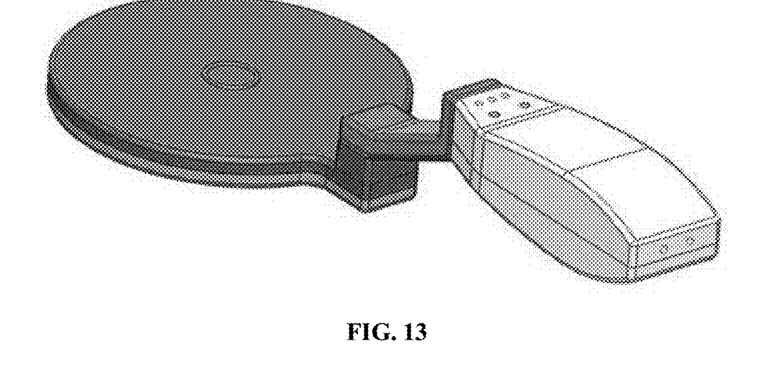
FIG. 13 is a schematic representation, in top view, of the identification device of retained surgical object.
Figure 14:
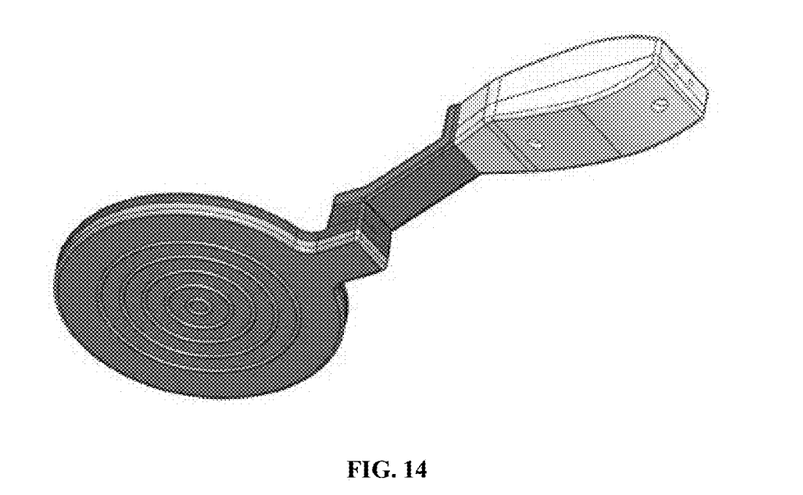
FIG. 14 is a schematic representation, in bottom view, of the identification device of retained surgical object.

Magnetic markers (4) represented in FIG. 6 can be sewn directly into the fabric, allowing preferably, the use of sewing or needlework machines for its application in fabrics, also allowing its application at manufacture time of surgical fabrics and gauze, with their incorporation in the manufacturing process in looms or in the health unit linen room.

For a better definition of the invention, "Surgical Object" can also be called "Surgical Instrument", and should be considered as any material that can be used in a surgery. Surgical objects may comprise two major groups: metallic and attached.

Metallic group may be, for example: forceps, scalpels, scissors, retractors, needle holder. Attached group may be, for example: dressing, gauze, drains, gloves, probes, catheters.

Retention Prevention System of Surgical Objects with Magnetic Markers

Retention prevention system of surgical objects with magnetic markers aims to provide instrumental support to the localization of retained surgical objects (5) in the interior of cavities of bodies to allow forgotten artifacts detection after a surgical procedure.

The referred system consists of a portable identification device (1); a recharge base; and surgical objects (5) with magnetic markers (4).

The identification system of retained surgical object (5) aims to provide instrumental support to the localization of retained surgical objects (5) in the interior of cavities of bodies to allow forgotten artifacts detection after a surgical procedure.

By means of the use of a system sensitive to magnetic fields, objects in the portable identification device (1) operating range, (magnetic markers (4) attached to surgical objects, (5) metallic or not), provoke a magnetic disturbance that is identified by the portable identification device (1).

By means of luminous and visual signalization, the user of the identification system can identify the presence of retained surgical objects (5) forgotten in patients after surgical procedure as follows: the sintered magnetic markers (4) emit constant magnetic field (6) over time; this magnetic field of magnetic markers (6) is detected by the portable identification device (1) that contains a sensing surface (3) with sensing elements (preferably, geomagnetic sensors).

The portable identification device (1) senses the perturbation in the magnetic field to which the sensing surface is subjected. This perturbation is then signaled by warning electronic device (2), located in the portable identification device (1) handhold (7), which generates visual and sonorous indicative signal of retained surgical object (5) presence in the interior of the patient.

In other words, said device, when subjected to the magnetic field of magnetic markers (4), is unbalanced and this signal unbalance is detected. In sequence, visual and sonorous signal is generated by electronic warning device (2), which drives sonorous and luminous alarms (8), indicating that there is a magnetic marker (4) and thus, there is a surgical object (5), at the place where the portable identification device (1) has passed.

Geomagnetic sensors are devices designed for utilization in applications related to positioning and geolocation. Their functioning is based on the variation of resistive characteristic of a material when exposed to magnetic fields. By means of an electrical circuit connected to this element, we can determine the intensity of the magnetic field applied to the device. Laying out magneto resistive elements in orthogonal disposition, we can thus obtain the magnetic field intensity applied to the object and thus determine the orientation of an object in this field. Geolocation applications use this type of device to implement digital electronic compasses, used in watches and other orientation guidance devices together with accelerometers and other positioning elements.

Present patent application introduces an innovative use of geomagnetic sensor for objects localization using magnetic markers in conjunction with combined arrays of geomagnetic sensor elements. Laying out an array of sensors in order to have its output information caused by magnetic field passing pairs of sensors in antagonistic orientation, we can have a resulting null signal from the x, y and z axes when the array is subjected to a uniform magnetic field, as the one generated by earth's magnetic field. In this condition, whatever the orientation of the array, the resulting electrical signal will be null.

Using a magnetic marker (4) that causes near its location a non-uniform magnetic field, antagonistic oriented pairs of sensors located in its vicinity will have different information from each other generating a non-zero resultant that will be used to indicate the presence of the magnetic marker (4). No matter the object location equipment relative position, with respect to the geomagnetic field, the presence of the marker is detected, by means of the presence of the non-uniform magnetic field generated by the marker.

Geomagnetic sensors have sensitivity to capture magnetic fields in the order of 0.1 uT (a tenth of micro Tesla) and can provide linear indication until the measuring limit of +/−1000 uT (more or less one thousand micro Tesla) entering saturation with fields above this value.

Magnetic markers based on neodymium-iron-boron to be used in conjunction with sensor equipment can generate magnetic fields in the order of up to 1.2 Tesla. Magnetic field decreases abruptly as we move away the sensor from the magnet poles and its field intensity is inversely proportional to the square of distance between them. In the objects localization application we can have distances up to 30 cm, between the portable identification device and the marker located in the interior of cavities of patients, being important the high sensitivity of array of sensors for the correct localization of the marker.

The processing software of the signals generated by the array of sensors is the responsible for the information treatment and measurement rules ensuring correct equipment operation as well as providing sonorous and visual indications of an easy to use portable equipment.

Utilization of the geomagnetic sensors in object localization as above described, allows the design of portable devices with low power consumption and high reliability.

Utilization of neodymium-iron-boron markers allows objects sterilization by means of autoclaves at temperatures above 150 degrees Celsius.

Utilization of magnetic markers can also be done in the localization of metallic iron objects for applications in accidents where objects may be inside the body of a patient due to an explosion and spreading of fragments and particles from a projectile, such as from grenade or projectile shot.

It is worth noting that the concept of prevention to which the retention prevention system refers to is related to the idea that a surgical object do not remain retained in the body of the patient after surgery, that is, in the post-surgery period. The invention does not prevent objects from being inserted into the patient's body but objects to be forgotten in the patient's body after a surgical procedure.

Identification Method of Surgical Objects with Magnetic Markers

Figure 15:
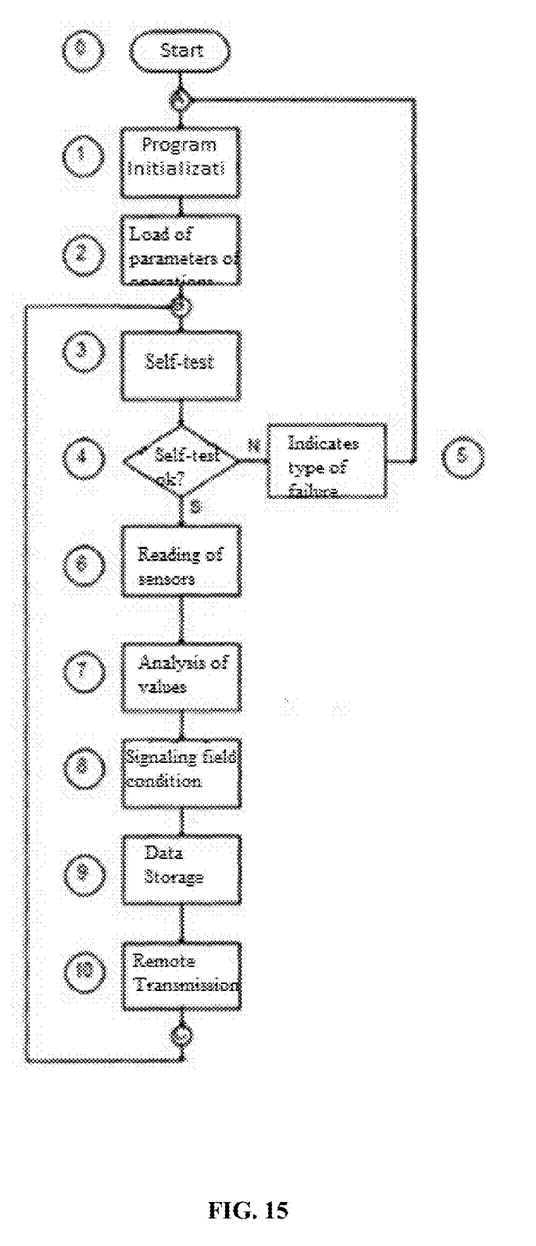
FIG. 15 is a representative technical flowchart of the operation of the identification method of the present invention, where: 0=start; 1=initialization program; 2=load of operating parameters; 3=self-test; 4=self-test ok?; 5=indicates type of failure; 6=reading of sensors; 7=analysis of values; 8=signaling of field condition; 9=data storage; 10=remote transmission.

FIG. 15 describes present invention representative technical flowchart. A programmable logic device responsible for the portable identification device operation (1), sequentially executes instructions stored in its program memory, by means of a software that implements the macro operations shown in the diagram of the referred FIG. 15.

The below description refers to the elements identified in the operations diagram of (flowchart) FIG. 15.

The Identification Method of Surgical Objects with Magnetic Markers Comprises the Following Steps:

0) Start;
1) Program initialization;
2) Load of operation parameters;
3) Self-test;
4) Self-test check;
6) Reading of Sensors;
7) Analysis of values;
8) Field condition signalization;
9) Data Storage; and
10) Remote transmission.

There may be a further optional step "5"—Indication of failure type, if there is any.

Step 0—

"Start" is the starting point of the sequential program execution and occurs when the key that provides power to the portable identifier device is driven. At this moment, an oscillator with stable frequency operation that serves as clock for the sequential execution of the of the portable identification device (1) operations, starts its operation and system components determine the operation beginning at a determined program condition where occurs the beginning of the instructions sequence that will execute the operations diagram shown in FIG. 1. The A element indicates the program point of operation restart that may occur in the event of occasion an error condition during portable identification device (1) self-test or in case of driving the key that turns on the power to the portable identification device (1) (Power or On-Off Switch).

Step 1—

Program initialization step: refers to the operations set intended to reload from storage memory of previous data the stored values after operation interruption for energy savings for portable identification device (1) internal power supply elements necessary before for the successful operation of the, properly setting up the portable identification device (1) programmable internal components, loading the values of variables necessary to perfect operation of portable identification device (1), i.e., from the rechargeable power supply or power storage element, for instance, a high capacity condenser and all small necessary operations in order to start the diagram next step.

Step 2—

Load of operation parameters step: and refers to the operations set that are intended to recover the memory storage of previous data values stored after the interruption of operation to save energy the internal power source of portable identification device (1), that is, the rechargeable power source (11) or energy storage element, for example, a capacitor of high capacity storage. The load of operation parameters step allows the operation of the portable identification device (1) to resume its operation from the point at which it was interrupted by power supply switched off or in the event of an appliance failure condition caused by several factors, for example, insufficient power for its operation. The data storage memory allows information retention even in the event of power failure, without any deterioration of its contents.

Step 3—

Self-test step: refers to the operations set intended to check the perfect operation condition of the portable identification device (1) prior to the beginning or restart of measurements step itself, and ensures that the measurements made by portable identification device (1) are within operating specifications. During the self-test phase various test results are stored to be used in the next step of the self-test check.

Step 4—

Self-test OK? Step: refers to the operations set that are intended to identify the self-test result in order to determine if the portable identification device (1) is in a condition to continue to step 5—Indication of failure type, if it is not in operating condition, or to step 6—Reading the Sensors, if it is in operating condition.

Step 5—

Indication of failure type step: is the operations set intended to indicate by means of signaling elements present in portable identification device (1), be it sonorous, visual, vibrational or combinations thereof that the device is not in operating condition and, therefore, should not be utilized until it is restored to operational condition. One of the signaled conditions is the lack of internal energy of portable identification device (1) power source. In the event of insufficient energy, be for the portable identification device (1) safe operation, this condition will be signaled and the portable identification device (1) power source must be recharged.

Step 6—

Reading of Sensors step: is the operations set that is intended to carry out the reading of the values from the various sensors present in the portable identification device (1) and that will be used to determine the presence of magnetic marker near the portable identification device (1). This is done by an array of geomagnetic sensors organized into a suitable array to be insensitive to the orientation of Earth's magnetic field and to detect the presence of a disturbance of a non-uniform magnetic field due to the marker. Optionally, auxiliary sensors, such as, for example, temperature, atmospheric pressure, operating voltage and altitude sensors, are used to allow calibration and linearization of magnetic field measurements. These sensors are also read by programmable logic device and the readings are stored in the nonvolatile data memory of portable identification device (1) for the next step of the operation.

Step 7—

Analysis of values step: is the operations set intended to do the validation operations of the performed readings, in order to ensure sensors readings quality and perform their treatment for compensation of environmental conditions of the place where the portable identification device (1) is located. At this step, the process of identifying marker presence is also carried out based on readings analysis, and the analysis result data is stored in the nonvolatile data memory of portable identification device (1) for the next step of operation.

Step 8—

Field condition signalization step: is the operations set intended to carry out the signaling operations of the magnetic marker presence, near the portable identification device (1) or not. Signalization is done through sonorous, luminous or vibrational elements or combinations thereof so as to indicate the field situation near the portable identification device (1) and this signalization varies dynamically as the field varies in the neighborhood of the portable identification device (1). Signalization is done based on results of the previous step and changes according to the result of sequential analysis during the operation.

Step 9—

Data storage step: is the operations set intended to store the contents of reading results during the operation of the portable identification device (1), for analysis or any operation requiring these results, for example, for transmission process to remote databases for evaluation or device calibration, among other operations. The data are stored in such a manner as to make efficient use of the storage capacity available in the portable identification device (1).

Step 10—

Remote transmission step: is the operations set intended to transmit, or not, operation information to an external element from portable identification device (1). This component enables the connection of the portable identification device (1) with a device manager or external data collector that can provide new operational features by means of indicating elements not available in the portable identification device (1), for example, video monitors where the field can be shown in graphical form with a wave form in time, among others.

After the completion of this step, the flow of portable identification device (1) sequential operations ends as indicated by the C point—and execution returns to B point.

Example of Invention Embodiment

Upon being driven the On/Off button (10) of the portable identification device (1), the boot process self-test sequence is started. In these first few seconds, the portable identification device (1) signalizes (4) by means of blinking red lights that tests are being carried out. At the end of the self-test, if the operating conditions are in accordance with the minimum parameters required, the identification device will indicate (4) through handhold light signalization, in green color, and will start the magnetic marker identification process. If, after testing, the operating conditions are not satisfactory, the red light indication (4) will remain constant and the portable identification device (1) should be turned off (3). To assist in the identification of the problem found during the self-test, a sequence of beeps (4) at intervals of 0.5 s will provide a beep sound. At the end of the sequence there is a pause of 2 s, restarting the sequence.

After the self-test, the portable identification device (1) enters the measurement procedure (5), seeking to identify the marker presence. While the magnetic field measured is within the threshold considered as normal, i.e., homogeneous distributed magnetic field, the portable identification device (1) will signalize (4) beeps with 0.2 s duration and 2 s cadence between the beeps. In addition, the luminous signal of green color (4) will be kept lit. In the presence of a magnetic marker, the beeps of 0.2 s will occur with smaller rhythms up to achieve maximum output of 0.4 s when the field reaches the maximum intensity. In addition, the luminous signalization will be changed from green (4) to 0.2 s blinking red with cadence ranging up to a maximum of 0.4 s. Additionally, a vibrational signalization device (4) will be activated indicating in a similar way the marker presence.

The purpose of the identification process is to ensure that each one of the objects from the list to be used in surgical procedure is previously identified by portable identification device (1) before it be used in a surgical procedure. Each one of the utensils should be placed close to the detection area and should be positively identified. The identification is made by means of signalization (4) presence when approaching the detector of the object to be identified. The identification of the marker presence is made by means of sonorous signal (4) in the form of beeps with variable cadence, by means of red light (4) and by means of vibration. When the object marker is moved away from the portable identification device (1), the beep sound cadence decreases, the light signalization changes from red to green and vibration ends.

Once made a positive identification of each object listed in the surgical procedure the portable identification device (1) should be turned off (3) to be used at the end of the surgical procedure. In this step, the identification of objects should be negative, i.e., when scanning for objects presence, no retained object should be found in the interior of the patient. On looking for the surgical object, if there is indication of presence, a seeking process should be made to find the marker that causes the indication.

The performed field measurements are stored in the internal memory (2) of the portable identification device (1) and may be transmitted by means of wireless communication devices (7) to a remote terminal where they can be stored or even used for location of objects by portable identification device (1) by means of graphical presentation on a computer display. Although the preferred version of the present patent application has been illustrated and described, it should be understood that this illustration is not limited. Various modifications, changes, variations, substitutions and equivalents may occur, without deviating from the scope of the present patent application.

The invention claimed is:

1. A portable device (1) for identification of a surgical object with a magnetic marker forgotten inside a patient characterized by comprising:
   (a) a sensing surface (3) comprising a probe, geomagnetic sensor elements, and an auxiliary sensor, the geomagnetic sensor elements being arranged in pairs of sensors in antagonistic orientation, wherein each pair of sensors is arranged on axes x, y, and z, so that an electrical signal, resulting from the arrangement of sensors on the axes x, y and z, is zero, in the presence of a uniform magnetic field, and a non zero electrical signal is generated in the presence of a non uniform magnetic field caused by the magnetic marker (4) that does not require external activation energy to operate, making the electrical signal available for measurement, and the auxiliary sensor compensating for environmental conditions surrounding the portable device, thereby increasing accuracy of the electrical signal; and
   (b) a microprocessed or microcontrolled system for the measurement of the electrical signal provided by the geomagnetic sensor arrangement; a programmable logic device for comparison of the electrical signal measured with security levels and confirmation of the disparity between the values; and a warning electronic device (2) located in a handhold (7), which activates a luminous and/or sound and/or vibration alarm, indicating the presence of the surgical object, wherein the microprocessed or microcontrolled system and the programmable logic device are located in the handhold; and
   (c) a rechargeable power source (11); wherein the portable device (1) is hermetic and contains a protective film of latex;
   wherein the sensing surface is associated with the handhold, where the electrical signal generated by the geomagnetic sensor comprised in the sensing surface is driven to the microprocessed or microcontrolled system.

2. The portable device according to claim 1 characterized in that the geomagnetic sensor elements have sensitivity to capture magnetic fields of an order of 0.1 micro Tesla, providing linear indication until a measuring limit of +/−1000 micro Tesla.

3. The portable device according to claim 1 characterized in that the rechargeable power source (11) comprises electrical circuits that have limitation of current load.

4. The portable device according to claim 1 characterized in that the warning electronic device (2) further activates an alarm that indicates that the probe of the sensing surface of the portable device is on; and/or that the rechargeable power source (11) is discharged.

5. The portable device according to claim 1 characterized in that the portable device further contains a button (10) to enable/disable the sound alarm (9).

6. The portable device according to claim 1 characterized in that the dimensions of the portable device range from 100×75×15 millimeter to 600×400×300 millimeter.

7. The portable device according to claim 1 characterized in that the portable device further comprises a stable frequency oscillator and microprocessed or microcontrolled system components, with the portable device operation starting upon oscillation start.

8. The portable device according to claim 1 characterized in that the portable device further comprises an operation program that restarts in an event of a failure condition during a self-test of the portable device, or when a key that provides power to the portable device is driven.

9. A system for preventing retention of a surgical object with a magnetic marker inside a patient characterized by comprising:
   (a) a portable device comprising: (i) a sensing surface (3) comprising a probe, geomagnetic sensor elements, and an auxiliary sensor, the geomagnetic sensor elements being arranged in pairs of sensors in antagonistic orientation, wherein each pair of sensors is arranged on axes x, y, and z generating electrical signal, whose generated electrical signal output resulting from the arrangement remains null under a uniform magnetic field, and provides a non null electrical signal output under the influence of a non uniform magnetic field such as the field generated by poles of the magnetic marker (4) that does not require external activation energy to operate, and the auxiliary sensor compensating for environmental conditions surrounding the portable device, thereby increasing accuracy of the electrical signal; (ii) a microprocessed or microcontrolled system for the measurement of the electrical signal; (iii) a programmable logic device for comparison of the non null measured electrical signal with security levels and confirmation of the disparity between the values; and (iv) a warning electronic device (2) located in a handhold (7), which activates a luminous and/or sound and/or vibration alarm, indicating the presence of the surgical object, wherein the microprocessed or microcontrolled system and the programmable logic device are located in the handhold; and
   (b) the magnetic marker (4) made of neodymium, iron, boron or a mixture thereof, being coated with a biocompatible acrylic resin and fixed to the surgical object (5) wherein said fixation is given by chemical adhesion, mechanical attachment, sewn or having been manufactured with fabrics;
   wherein the sensing surface is associated with the handhold, where the electrical signal generated by the geomagnetic sensor comprised in the sensing surface is driven to the microprocessed or microcontrolled system.

10. The system for preventing retention of a surgical object with a magnetic marker according to claim 9 characterized in that the geomagnetic sensor elements have sensitivity to capture magnetic fields of an order of 0.1 micro Tesla, providing linear indication until a measuring limit of +/−1000 micro Tesla.

11. The system for preventing retention of a surgical object with a magnetic marker according to claim 9 characterized in that the retained object (5) is detectable at distances up to 30 centimeter between the portable device (1) and the magnetic marker (4) located within cavities of patients.

12. A method of identification of a surgical object with a magnetic marker forgotten inside a patient characterized by comprising the use of a portable device comprising a sensing surface (3) comprising a probe, geomagnetic sensor elements, and an auxiliary sensor, for the detection of the magnetic marker (4) of neodymium, iron, boron or a mixture thereof, being coated with a biocompatible acrylic resin, and including the fixation in surgical objects (5) accession by chemical, mechanical, or manufactured with fabrics or sewn, comprising the steps of:
   (a) positive identification, prior to a surgical procedure, of all surgical objects to be used in the surgical procedure;

(b) generating an electrical signal by the geomagnetic sensors arranged in pairs of sensors in antagonistic orientation, wherein each pair of sensors is arranged on axes x, y, and z;
(c) generating a compensating signal by the auxiliary sensor compensating for environmental conditions surrounding the portable device, thereby increasing accuracy of the electrical signal;
(d) scanning with the sensing surface (3) for detection and alarm of any objects forgotten in the interior of cavities of patients; and
(e) signaling by a warning electronic device (2) when a non zero electrical signal is generated by a perturbation caused by the magnetic marker (4) being sensed by the sensing surface (3).

* * * * *